United States Patent
Shumer et al.

(10) Patent No.: US 9,326,875 B2
(45) Date of Patent: *May 3, 2016

(54) CATHETER HAVING A MOVABLE TUBULAR STRUCTURE AND METHOD OF MAKING

(71) Applicant: Abbott Cardiovascular Systems Inc., Santa Clara, CA (US)

(72) Inventors: Daniel H. Shumer, San Jose, CA (US); Nianjiong Joan Bei, Palo Alto, CA (US); Marc Gianotti, Wiesendangen (CH); Ana Montano-Morse, Union City, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 353 days.

This patent is subject to a terminal disclaimer.

(21) Appl. No.: 13/801,588

(22) Filed: Mar. 13, 2013

(65) Prior Publication Data

US 2014/0276412 A1    Sep. 18, 2014

(51) Int. Cl.
*A61F 2/95* (2013.01)
*A61F 2/966* (2013.01)
*A61M 25/00* (2006.01)
*A61M 25/01* (2006.01)
(Continued)

(52) U.S. Cl.
CPC ............ *A61F 2/966* (2013.01); *A61M 25/0009* (2013.01); *A61M 25/0122* (2013.01); *A61F 2/95* (2013.01); *A61F 2/962* (2013.01); *A61F 2250/0029* (2013.01); *A61M 25/005* (2013.01); *A61M 25/0012* (2013.01); *A61M 25/0108* (2013.01); *A61M 2025/0175* (2013.01); *A61M 2025/0681* (2013.01); *Y10T 29/49826* (2015.01)

(58) Field of Classification Search
CPC ....... A61F 2/966; A61F 2/962; A61F 2/2436; A61F 2/2409; A61F 2/2418; A61M 2025/0175; A61M 2025/0681; A61M 2025/0018; A61M 25/0009; A61M 25/0013; A61M 25/0021; A61M 25/0043; A61M 25/0067; A61M 25/0122
See application file for complete search history.

(56) References Cited

U.S. PATENT DOCUMENTS 5,695,468 A  12/1997  Lafontaine et al.
5,709,703 A   1/1998  Lukic et al.
(Continued)

OTHER PUBLICATIONS

International Search Report for PCT/US2013/068306, dated Jan. 8, 2014.
(Continued)

*Primary Examiner* — Christopher L Templeton
(74) *Attorney, Agent, or Firm* — Baker Botts L.L.P.

(57) ABSTRACT

Catheter including an inner tubular member having a proximal end portion, a distal end portion and an exterior surface. The inner tubular member further has a guidewire lumen defined therein. An outer tubular member is movable relative to the inner tubular member, the outer tubular member has a proximal end, a distal end and an interior surface directed toward the exterior surface of the inner tubular member. A movable tubular structure is disposed between the outer tubular member and the inner tubular member. The movable tubular structure includes a body member having an outer surface with a recess defined therein. The outer tubular member is received within the recess to form a trough along a portion of an exterior surface of the outer tubular member. The trough has a filler disposed therein to couple the outer tubular member to the body member of the movable tubular structure.

37 Claims, 11 Drawing Sheets

(51) Int. Cl.
*A61F 2/962* (2013.01)
*A61M 25/06* (2006.01)

(56) References Cited

U.S. PATENT DOCUMENTS

| | | | |
|---|---|---|---|
| 5,776,141 A | 7/1998 | Klein et al. | |
| 5,817,101 A | 10/1998 | Fiedler | |
| 6,056,759 A * | 5/2000 | Fiedler | 623/1.11 |
| 6,113,608 A | 9/2000 | Monroe et al. | |
| 6,214,037 B1 | 4/2001 | Mitchell et al. | |
| 6,287,285 B1 | 9/2001 | Michal et al. | |
| 6,425,898 B1 | 7/2002 | Wilson et al. | |
| 6,541,116 B2 | 4/2003 | Michal et al. | |
| 6,605,109 B2 | 8/2003 | Fiedler | |
| 6,884,257 B1 * | 4/2005 | Cox | 623/1.11 |
| 6,945,989 B1 * | 9/2005 | Betelia et al. | 623/1.11 |
| 7,740,652 B2 | 6/2010 | Gerdts et al. | |
| 7,799,065 B2 | 9/2010 | Pappas | |
| 8,435,279 B2 | 5/2013 | Beyerlein et al. | |
| 8,685,076 B2 | 4/2014 | Gerdts et al. | |
| 9,011,513 B2 | 4/2015 | Bialas et al. | |
| 2001/0027323 A1 * | 10/2001 | Sullivan, III | A61F 2/95 606/108 |
| 2002/0009535 A1 | 1/2002 | Michal et al. | |
| 2002/0045929 A1 | 4/2002 | Diaz | |
| 2002/0058951 A1 | 5/2002 | Fiedler | |
| 2004/0193178 A1 | 9/2004 | Nikolchev | |
| 2004/0193243 A1 | 9/2004 | Mangiardi et al. | |
| 2007/0078506 A1 * | 4/2007 | McCormick et al. | 623/1.11 |
| 2007/0123971 A1 | 5/2007 | Kennedy et al. | |
| 2008/0294230 A1 | 11/2008 | Parker | |
| 2009/0018529 A1 | 1/2009 | Hoffman et al. | |
| 2009/0204197 A1 | 8/2009 | Dorn et al. | |
| 2009/0292262 A1 | 11/2009 | Adams et al. | |
| 2009/0312832 A1 | 12/2009 | Delap | |
| 2010/0087906 A1 * | 4/2010 | Dorn | A61F 2/966 623/1.11 |
| 2010/0286756 A1 * | 11/2010 | Dorn | A61F 2/95 623/1.11 |
| 2011/0307049 A1 | 12/2011 | Kao | |
| 2013/0073024 A1 * | 3/2013 | Russo et al. | 623/1.11 |
| 2013/0297011 A1 * | 11/2013 | Morris et al. | 623/2.11 |
| 2013/0304180 A1 | 11/2013 | Green et al. | |
| 2013/0304181 A1 | 11/2013 | Green et al. | |
| 2014/0194969 A1 | 7/2014 | Headley | |
| 2014/0214151 A1 * | 7/2014 | Ibeling | 623/2.11 |
| 2014/0277356 A1 | 9/2014 | Shumer et al. | |

OTHER PUBLICATIONS

International Search Report for PCT/US2013/030830, dated Jan. 15, 2014.
U.S. Appl. No. 13/467,679, Aug. 22, 2014 Restriction Requirement.
International Search Report and Written Opinion for PCT/US2013/036881, dated Aug. 2, 2013.
International Search Report and Written Opinion for PCT/US2013/036884, dated Aug. 2, 2013.
International Search Report and Written Opinion for PCT/US2013/030513, dated Aug. 2, 2013.
U.S. Appl. No. 13/467,660, Oct. 7, 2013 Non-Final Office Action.
U.S. Appl. No. 13/467,660, Jan. 4, 2014 Response to Non-Final Office Action.
International Search Report and Written Opinion for PCT/US2013/069477, dated Jan. 8, 2014.
U.S. Appl. No. 13/467,660, Jul. 17, 2014 Final Office Action.
U.S. Appl. No. 13/797,636, Dec. 10, 2015 Notice of Allowance.
U.S. Appl. No. 14/767,968, Dec. 10, 2015 Notice of Allowance.
U.S. Appl. No. 13/797,636, filed Mar. 12, 2013.
U.S. Appl. No. 13/467,660, filed May 9, 2012.
U.S. Appl. No. 13/467,679, filed May 9, 2012.
U.S. Appl. No. 13/467,715, filed May 9, 2012.
U.S. Appl. No. 14/653,582, filed Jun. 18, 2015.
U.S. Appl. No. 14/767,968, filed Aug. 14, 2015.
U.S. Appl. No. 13/797,636, Jun. 30, 2015 Non-Final Office Action.
U.S. Appl. No. 13/797,636, Oct. 30, 2015 Response to Non-Final Office Action.
U.S. Appl. No. 13/467,660, Oct. 14, 2014 Response after Final Action.
U.S. Appl. No. 13/467,660, Nov. 25, 2014 Notice of Allowance.
U.S. Appl. No. 13/467,660, Feb. 25, 2015 Issue Fee Payment.

* cited by examiner

CATHETER HAVING A MOVABLE TUBULAR STRUCTURE AND METHOD OF MAKING

BACKGROUND OF THE DISCLOSED SUBJECT MATTER

1. Field of the Disclosed Subject Matter

The disclosed subject matter relates to catheters used in the delivery of medical devices such as self-expanding stents for treating the luminal systems of a patient. Specifically, the disclosed subject matter relates to a delivery catheter having a retractable sheath moved by a hydraulic actuator.

2. Description of the Related Art

A variety of systems using a retractable sheath are known for intraluminal delivery of a medical device, such as a stent or filter. However, there remains a need for continued improvement of such known delivery systems.

An example of such a system is described in U.S. Pat. No. 6,425,898 to Wilson et al., which is incorporated by reference herein, wherein a delivery system is provided having an inner member with a stop attached to the inner member. During deployment, the stop prevents the stent from migrating proximally during retraction of the sheath for stent deployment.

Conventional self-expanding stent delivery systems generally comprise a handle portion and an elongated shaft, wherein the stent is disposed within a delivery portion at the distal end of the shaft. To deploy the stent, an outer sheath is provided which can be retracted relative to the stent to release the stent from its delivery configuration. The sheath in such systems generally spans the full length of the catheter resulting in an increased profile and stiffness over the entire length of the catheter. Such stiffness and increased profile at the distal end of the catheter can restrict certain applications, such as neuro and other indications of particular size limitations. Further, because the sheath spans the full length of the catheter there is an increased risk of the sheath binding with other components of the catheter during passage through the tortuous luminal system of a patient, thus inhibiting the deployment of the stent.

Another issue with such delivery systems is that the sheath is generally pulled back in a 1-to-1 ratio with the user's input (force). Because the stent may embed in the outer sheath during storage and shipping, and due to larger static friction forces, a large amount of initial input is typically required to release the stent which may lead to incorrect placement. When initially releasing the stent, it may be desirable to slowly pull back the sheath for proper placement and then more readily retract the sheath to prevent inadvertent movement of the stent.

Further, the amount of force that is required to retract the sheath, particularly for stents of greater length as required for peripheral indications, can be substantial. To overcome this issue, a lubricious liner can be used to decrease the amount of force required to retract the sheath. However, there remains a need for an improved delivery system for self-expanding stents having reduced force requirements for delivery of a self-expanding stent or the like.

There thus remains a continued need for an efficient and economic system for delivering a medical device that is easy to use and provides accurate placement. The presently disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes a catheter comprising, among other things, an inner tubular member having a proximal end portion, a distal end portion and an exterior surface, the inner tubular member further having a guidewire lumen defined therein; an outer tubular member movable relative to the inner tubular member, the outer tubular member having a proximal end, a distal end and an interior surface directed toward the exterior surface of the inner tubular member; and a movable tubular structure disposed between the outer tubular member and the inner tubular member, the movable tubular structure comprising a body member having an outer surface with a recess defined therein, the outer tubular member received within the recess to form a trough along a portion of an exterior surface of the outer tubular member, the trough having a filler disposed therein to couple the outer tubular member to the body member of the movable tubular structure.

In accordance with another aspect of the disclosed subject matter, a method of making a catheter comprising, among other things, providing an inner tubular member having a proximal end portion, a distal end portion and an exterior surface, the inner tubular member further having a guidewire lumen defined therein; providing an outer tubular member movable relative to the inner tubular member, the outer tubular member having a proximal end, a distal end and an interior surface directed toward the exterior surface of the inner tubular member; locating a movable tubular structure between the outer tubular member and the inner tubular member, the movable tubular structure comprising a body member having an outer surface with a recess defined therein, the outer tubular member being received within the recess to form a trough along a portion of an exterior surface of the outer tubular member; and disposing a filler in the trough, the filler having a suitable hoop strength to couple the outer tubular member to the body member of the movable tubular structure.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 7A is a cross sectional view of the catheter of FIG. 7 taken at line 7A.

DETAILED DESCRIPTION

Reference will now be made in detail to embodiments of the disclosed subject matter, an example of which is illustrated in the accompanying drawings. The disclosed subject matter will be described in conjunction with the detailed description of the system.

As disclosed herein, the devices presented herein can be used for treating the luminal system of a patient. In particular, the disclosed subject matter is particularly suited for treatment of cardiovascular and the peripheral systems of a patient.

In accordance with the disclosed subject matter, a catheter is provided comprising, among other things, an inner tubular member having a proximal end portion, a distal end portion and an exterior surface, the inner tubular member further having a guidewire lumen defined therein; and an outer tubular member movable relative to the inner tubular member, the outer tubular member having a proximal end, a distal end and an interior surface directed toward the exterior surface of the inner tubular member. The catheter further comprises a movable tubular structure disposed between the outer tubular member and the inner tubular member, the movable tubular structure comprising a body member having an outer surface with a recess defined therein, wherein the outer tubular member is received within the recess to form a trough along a portion of an exterior surface of the outer tubular member. The trough has a filler disposed therein to couple the outer tubular member to the body member of the movable tubular structure.

Figure 1:
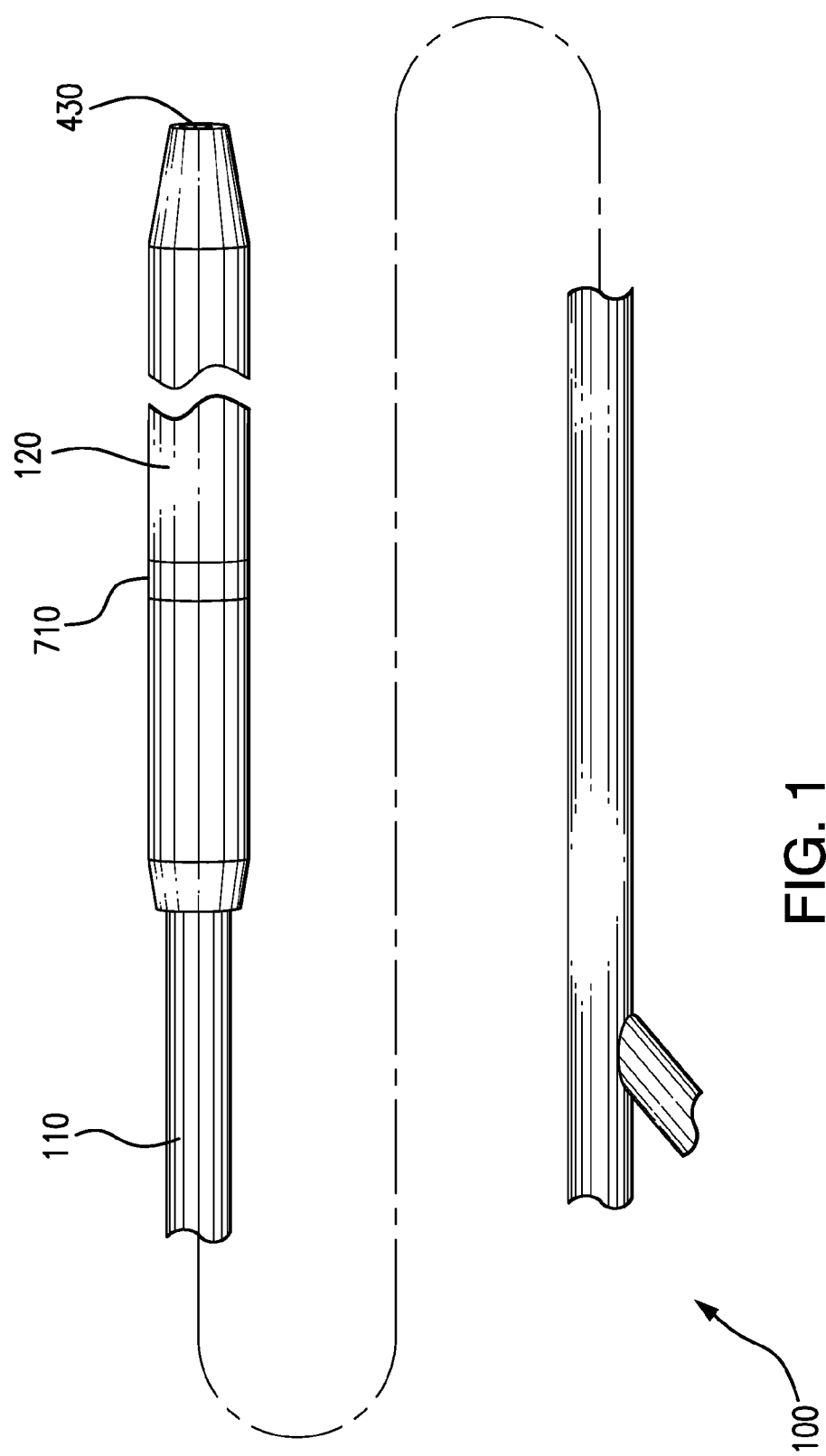
FIG. 1 is a schematic side view of a representative catheter in accordance with the disclosed subject matter.
Figure 2:
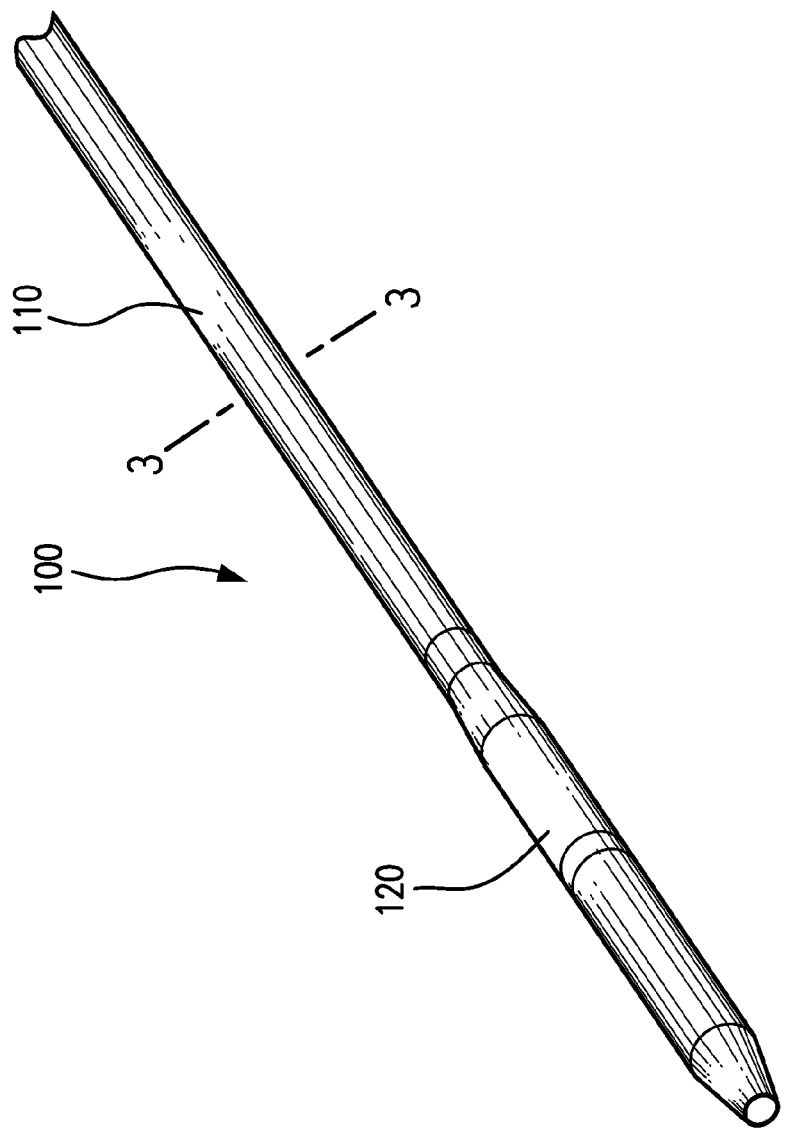
FIG. 2 is a perspective view of the distal end section of the catheter of FIG. 1.

Solely for purpose of illustration, an exemplary embodiment of a hydraulic delivery system for a self-expanding stent or the like, is shown schematically in FIGS. 1 and 2. The examples herein are not intended to limit the scope of the disclosed subject matter in any manner. Particularly, and as illustrated, the hydraulic delivery system embodied herein is a catheter 100 for cardiovascular intervention or the like, Catheters for other interventions, such as peripheral and below the knee interventions, are contemplated herein. The catheter 100 includes an inner tubular member 110 having a proximal end portion, a distal end portion, and an exterior surface. The catheter 100 further includes an outer tubular member or sheath 120 which is movable relative to the inner tubular member 110 and has a proximal end, a distal end and an interior surface directed toward the exterior surface of the inner tubular member 110. As shown in FIG. 2, the outer tubular member 120 is disposed only at a distal end portion of the catheter in this embodiment. For other embodiments, the outer tubular member 120 can be disposed at the proximal end portion and/or the distal end portion of the catheter. As described further herein, the catheter of the disclosed subject matter can be configured to deliver a medical device, such as a stent, of any suitable length. That is, the catheter can be configured to generate a force sufficient to retract the outer tubular member, wherein the generated force is greater than the resistance force caused by the medical device acting on the outer tubular member.

Figure 3A:
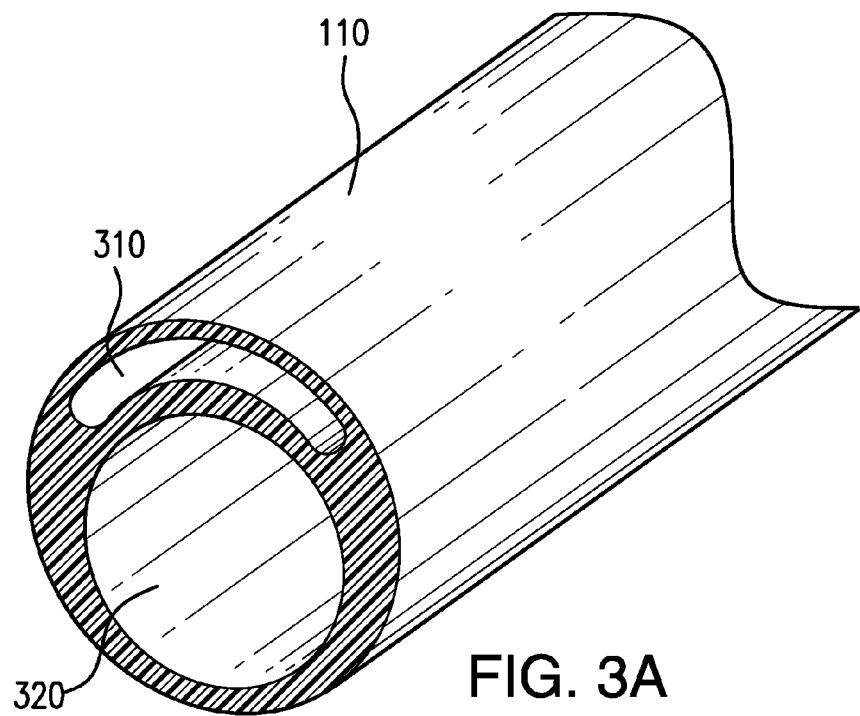
FIG. 3A is a cross sectional perspective view of the catheter of FIG. 2 taken along line 3-3.

Solely for purpose of illustration, reference is made to FIG. 3A which depicts a representative cross sectional view of an exemplary inner tubular member 110 along lines 3-3 of FIG. 2, in accordance with the disclosed subject matter. The inner tubular member 110 further has a fluid lumen 310 defined therein. In one embodiment the inner tubular member can also have a guidewire lumen 320 defined at least along a length therein. For example, the guidewire lumen 320, if provided, can extend over the entire length of the inner tubular member 110 such as for an "over-the-wire" configuration, or only along a distal length such as for a "rapid exchange" embodiment. Alternatively the catheter 100 can have a single-lumen design and the guidewire and pressurized fluid can share the same lumen (not shown), wherein a seal or valve can be provided at distal and proximal ends.

Figure 3B:
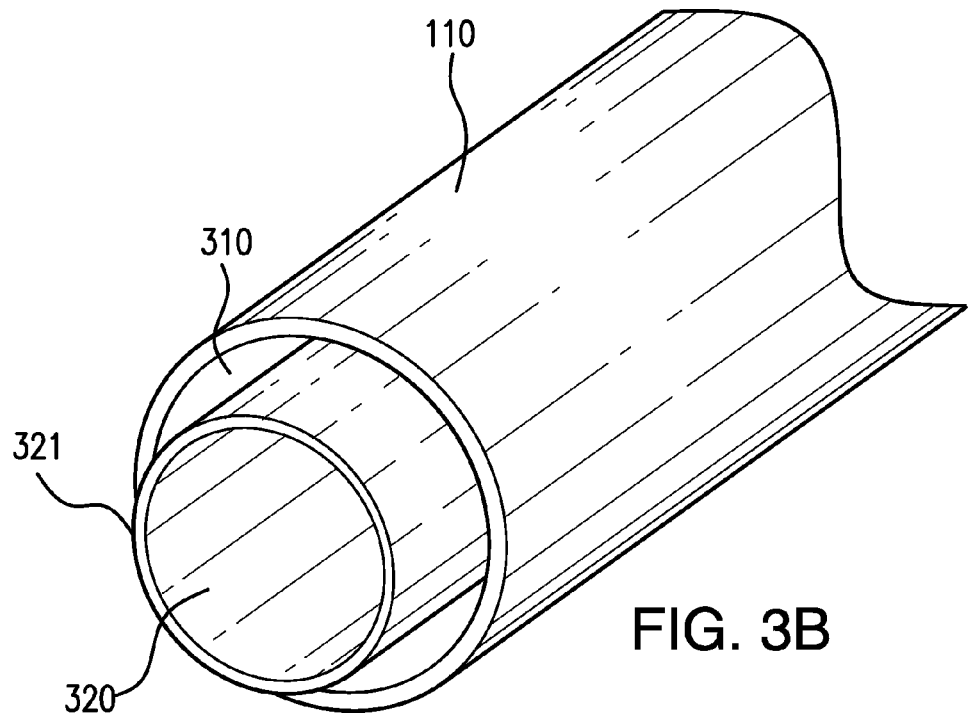
FIG. 3B is a cross sectional perspective view of another embodiment of the catheter of FIG. 2 taken along line 3-3.

FIG. 3B depicts another embodiment of a representative cross sectional view of an exemplary inner tubular member 110 along lines 3-3 of FIG. 2. In this embodiment, as shown in FIG. 3B solely for purposes of illustration, the guidewire lumen 320 can be defined at least in part by a separate guidewire tube 321 disposed within a fluid lumen 310 and sealed at either side, such as for example, by a marker (not shown). Such coaxial configurations allow for reduced diameter of the inner tubular member 110, and thus reduced profile. Indeed the guidewire tube 321 defining the guidewire lumen 320 can be formed by a thin membrane of suitable strength to prevent the guidewire from penetrating therethrough. Hydraulic fluid can thus flow within the fluid lumen 310 but outside the guidewire lumen 320.

Figure 4:
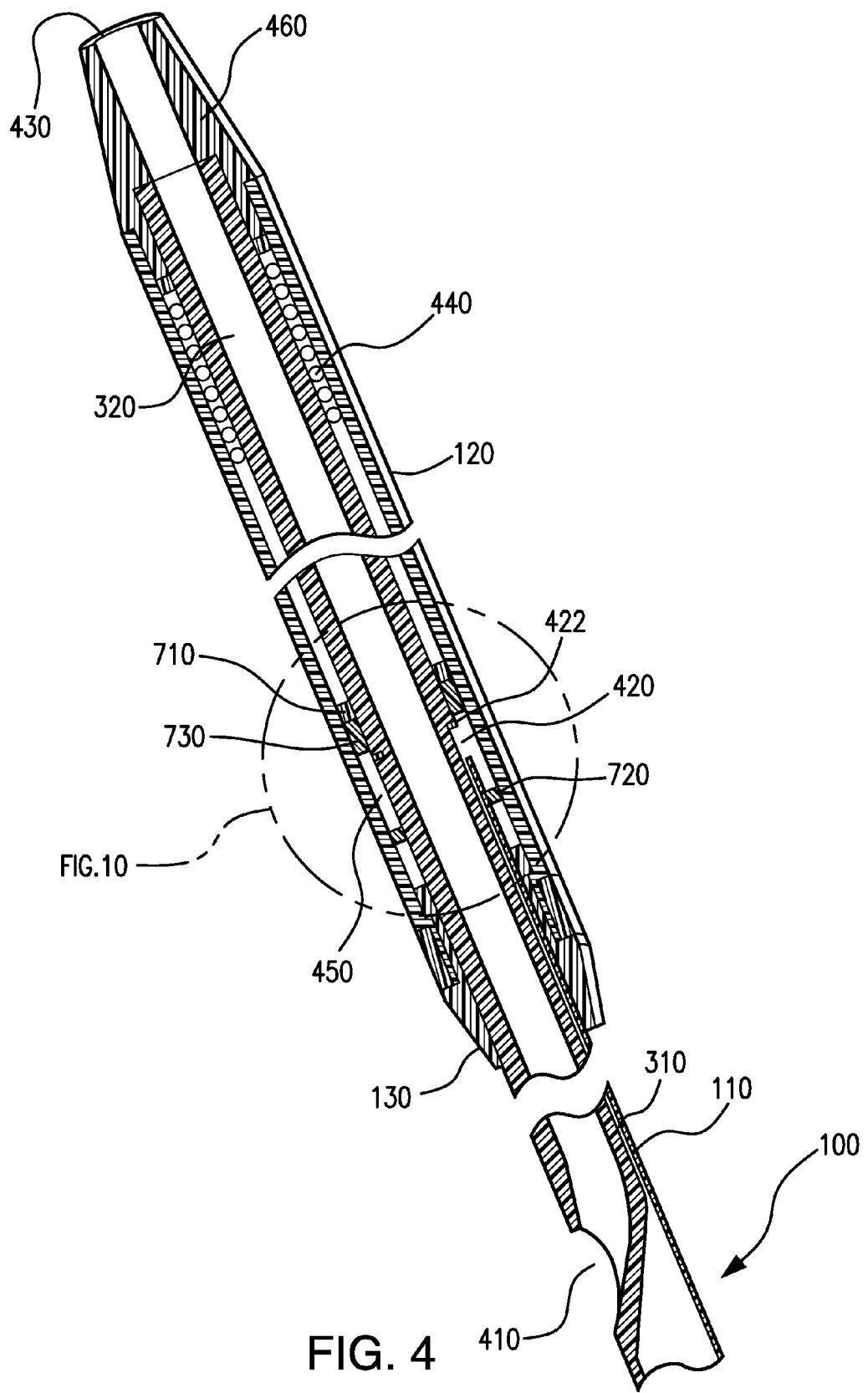
FIG. 4 is a cross sectional perspective side view of the distal end section of a catheter in accordance with the disclosed subject matter with the sheath in a closed position.

Solely for purpose of illustration, reference is now made to a rapid exchange configuration of the catheter disclosed herein as shown in FIG. 4. Generally, the catheter includes an inner tubular member 110 having a proximal end portion, a distal end portion and an exterior surface. The inner tubular member 110 further includes a fluid lumen 310 having a fluid flow port 420 defined by the exterior surface 111 along a distal end portion of inner tubular member 110. The outer tubular member 120 is movable relative to the inner tubular member 110 and has a proximal end, a distal end and an interior surface 121 directed toward the exterior surface 111 of the inner tubular member 110. As described in more detail below, the fluid flow port 420 allows fluid to pass from within fluid lumen 310 into the space defined by the inner tubular member 110 and outer tubular member 120 for operation and retraction of the outer tubular member 120. A marker 422 can define the distal end of the fluid flow port 420. As embodied herein, the rapid exchange catheter further includes guidewire lumen 320 extending along a distal end portion of the catheter and including a proximal guidewire port 410 and a distal guidewire port 430.

Figure 6:
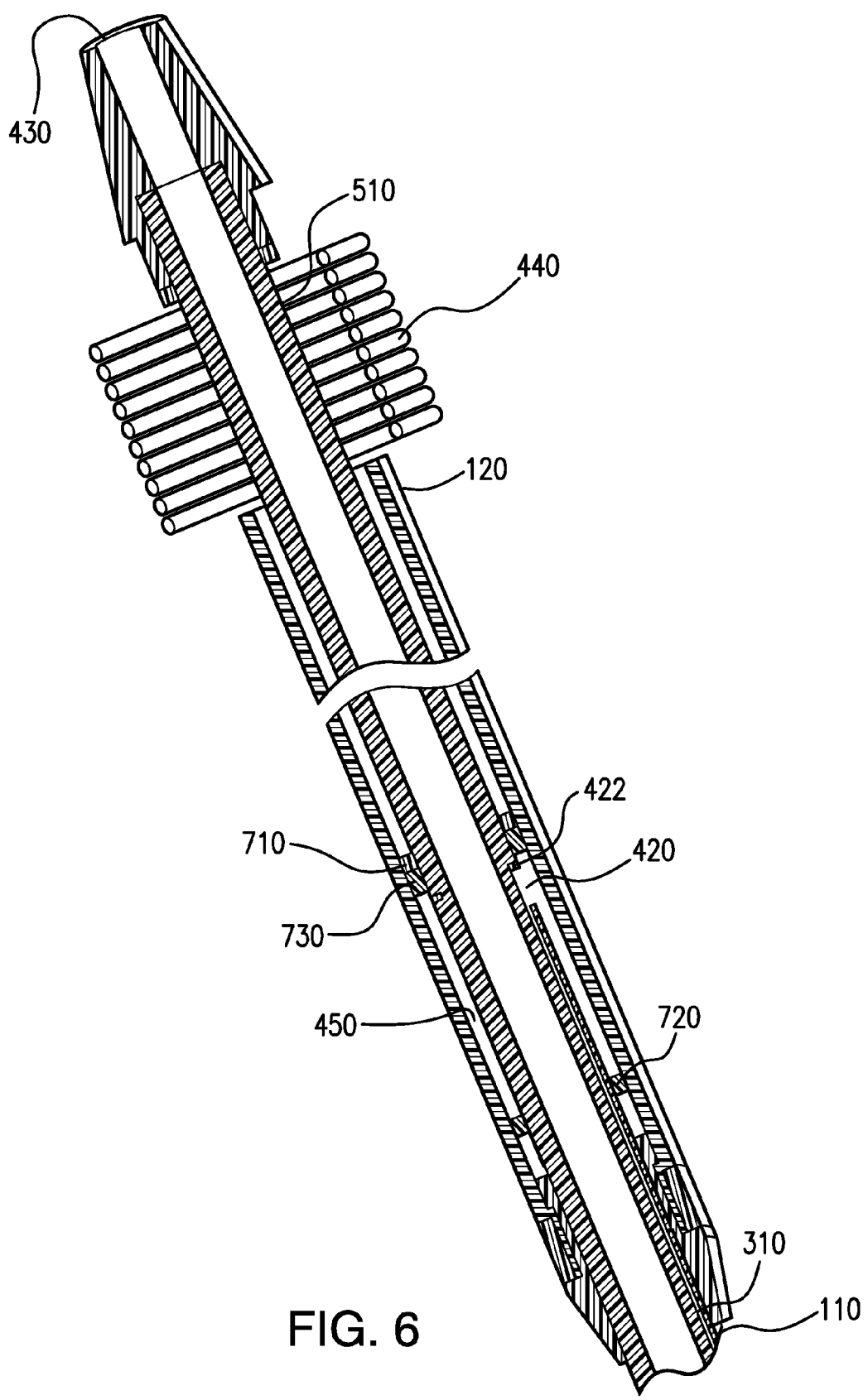
FIG. 6 is a cross sectional side view of the distal end of the catheter of FIG. 4 with the sheath in a fully retracted position.
Figure 7:
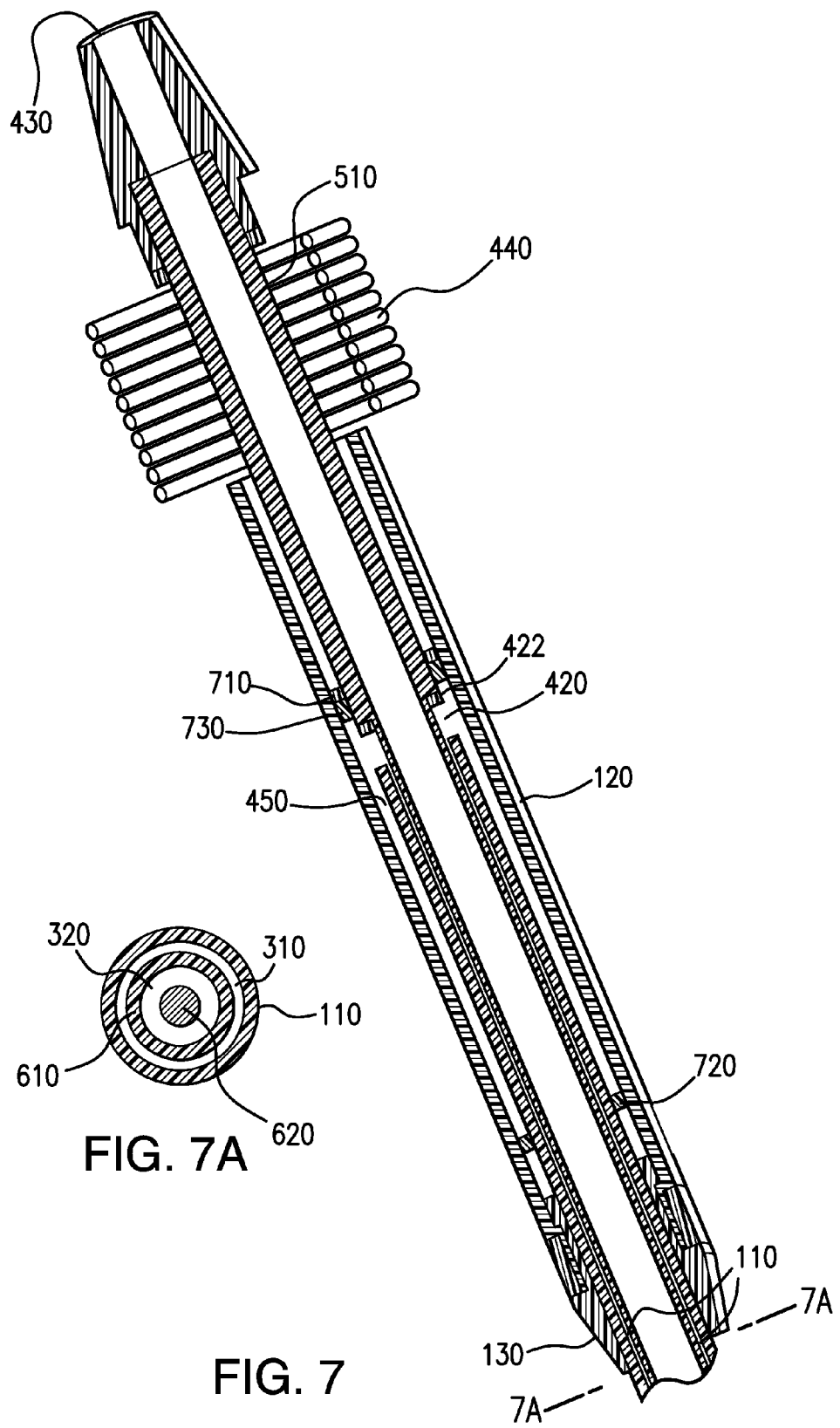
FIG. 7 is a cross sectional side view of the distal end section of an alternative catheter in accordance with the disclosed subject matter with the sheath in a fully retracted position.

As illustrated, the outer tubular member 120 can be moved from an extended position as shown in FIG. 4 to a retracted position shown in FIG. 6. When extended, the outer tubular member 120 retains a medical device, such as a stent 440 as depicted herein, in a compressed or delivery condition. A distal tip 460 can also be provided at a distal end of the inner tubular member 110 to further enclose the medical device during delivery. When the outer tubular member 120 is retracted (as shown in FIGS. 6 and 7), the medical device is unsheathed and allowed to expand to a deployed condition.

In accordance with the disclosed subject matter and as depicted in FIGS. 4-7, the outer tubular member 120 further includes at least one movable tubular structure 130 is disposed between the outer tubular member 120 and the inner tubular member 110. With reference to FIGS. 5A and 5B, a detailed view of the movable tubular structure 130 is provided, according to a representative embodiment of the subject matter. The movable tubular structure 130 generally comprises a body member 131 with an outer surface having a recess 134 defined therein. As further shown in FIG. 5A, and as embodied herein, the body member 131 includes a taper segment 132 and a base segment 133. FIG. 5A shown, for purposes of illustration, the recess 134 is disposed in the base segment 133 of the body member 131. Alternative embodiments of the disclosed subject matter likewise include one or more recesses in the taper segment 132 and/or one or more recesses in the base segment 133. For example, FIG. 5C depicts a movable tubular structure 130 having a recess 134 being disposed in the taper segment 132 of the body member 131 and additional recesses 134A and 134B being disposed in the base segment 133.

Figure 5A:
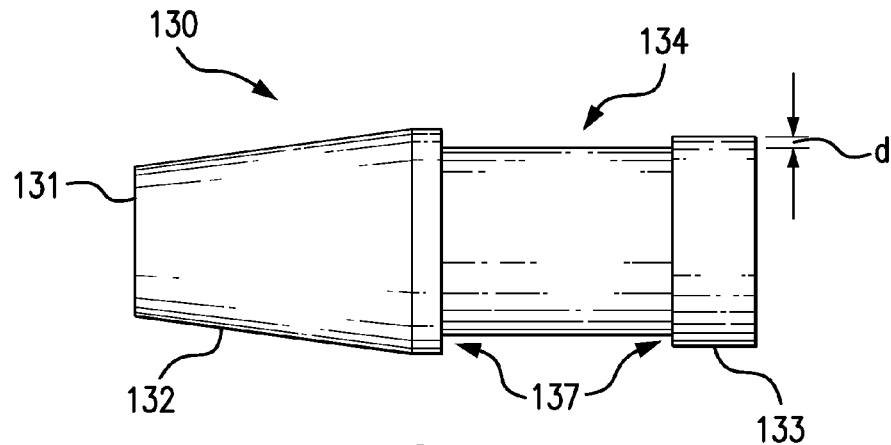
FIG. 5A is a detailed view of a movable tubular structure in accordance with a representative embodiment of the disclosed subject matter.

As disclosed herein, the recess 134 can be defined at least in part by at least one shoulder 137 proximate the outer surface to the body member 131. The shoulder 137 has an angle relative the outer surface of the body member 131. The angle of the shoulder relative the outer surface can range from approximately 70 degrees to approximately 110 degrees. For example, without limitation, as depicted in FIG. 5A, a shoulder 137 can be formed at each end of the recess, with the angle of each shoulder shown as substantially perpendicular. Furthermore, the recess has a depth d of any suitable dimensions. For example, with reference to FIG. 5A and FIG. 5B, the depth d of the recess 134 can be approximately equal to or greater than a thickness t of the outer tubular member 120. For example, and with reference to a cardiovascular catheter, the thickness t of the outer tubular member 120 is between approximately 0.0025 inches to 0.0035 inches. The depth d can generally range from approximately 0.002 inches to 0.006 inches. Other feasible dimensions for the thickness t and corresponding depth d can be permitted.

Figure 5B:
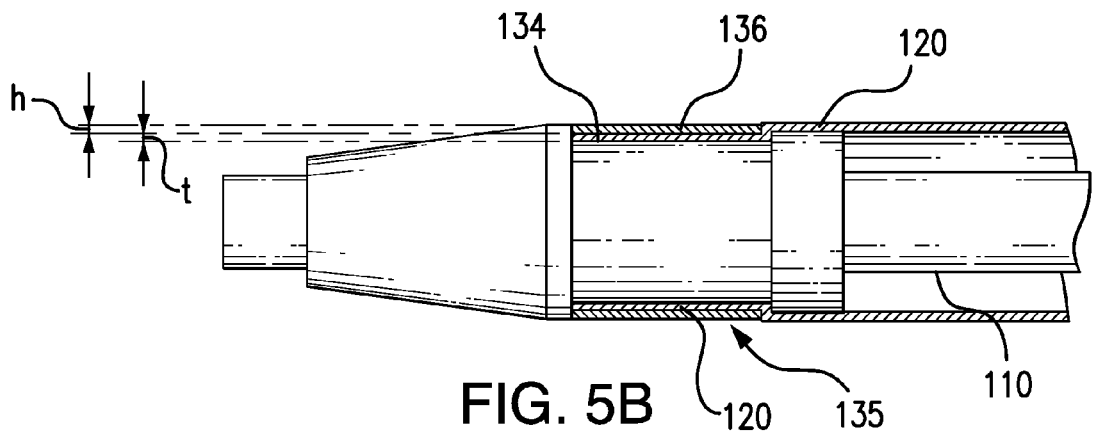
FIG. 5B is a detailed view of a catheter with the movable tubular structure of FIG. 5A in accordance with the disclosed subject matter.
Figure 5C:
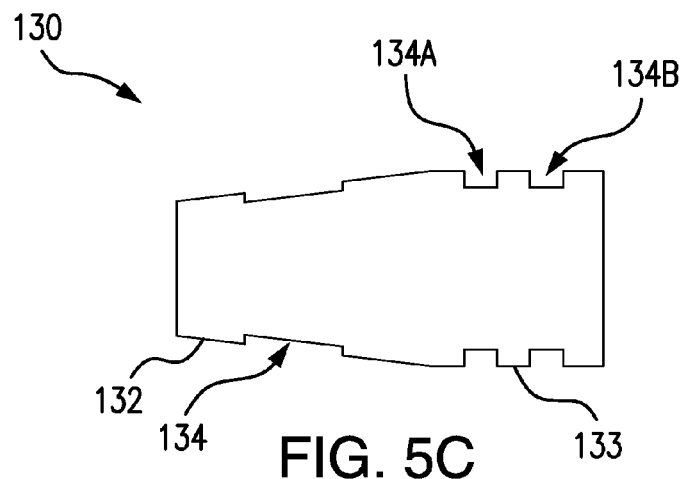
FIG. 5C is a detailed view of another representative embodiment of the movable tubular structure in accordance the disclosed subject matter.

As depicted in FIG. 5B, and in accordance with the disclosed subject matter, the outer tubular member 120 is received within the recess 134 to form a trough 135 along a portion of an exterior surface of the outer tubular member 120. If more than one recess is provided, a second portion of the outer tubular member can be received within the second recess to form a second trough.

As disclosed herein, and in accordance with the disclosed subject matter, the trough 135 has a filler 136 disposed therein to couple the outer tubular member 120 to the body member 131 of the movable tubular structure 130. As embodied herein the filler 136 generally can have a thickness h equal to the depth d of the recess 134. Accordingly, and with reference to the exemplary dimensions above, the thickness h of the filler can range from approximately 0.002 inches to approximately 0.006 inches.

As embodied herein, an exterior surface of the filler 136 is substantially flush with an exterior surface of the outer tubular member 120 adjacent the recess 134. In this manner and as shown in FIG. 5B, a transition between the exterior surface of the filler 136 and the exterior surface of outer tubular member 120 adjacent the recess 134 is substantially smooth. Furthermore, the filler is provided with additional hoop strength to secure the portion of outer tubular member within the recess of the moveable tubular structure. As depicted in FIG. 5B, the filler 136 also abuts the shoulder 137 of the movable tubular structure 130 with the outer tubular member sandwiched therebetween to create the grip and lock. The movable tubular structure 130 and the outer tubular member 120 are thus locked together by the filler 136. Since the outer tubular member 120 is movable with respect to the inner tubular member 110, the movable tubular structure 130 moves with the outer tubular member 120.

The filler can be any suitable material capable of providing sufficient hoop strength to couple the outer tubular member with the recess of the movable tubular member. For example, the filler can comprise at least one of nylon, fluoropolymer, peek, epoxy, platinum iridium, ceramic or metal, such as a metal band or the like. In accordance with a particular aspect of the disclosed subject matter, the filler comprises a material compatible for thermal bonding with a material of the outer tubular member. For example, the material of the filler can comprise the same material as the outer tubular member. The compatibility of the filler and the outer tubular member thus allows for a more secure lock between the outer tubular member and the moveable tubular structure, even if the outer tubular member is not thermally compatible with the movable tubular structure. Additionally, the increased thickness of outer tubular member and filler bonded together with the recess provides a strength that a single layer material does not inherently comprise. Further, a substantially continuous surface of the adjacent outer tubular member with the filler is provided by the heat bond to eliminate an area or edge that could potentially catch while the system is being advanced or withdrawn from the vasculature. Additionally, the mechanical lock created by the filler provides the strength to maintain the integrity of the catheter components. The filler thus can bonded to the outer tubular member by at least one of heat bonding, thermal bonding, adhesive bonding, or the like, as well as by crimping or swaging of a bond of suitable material.

Figure 8:
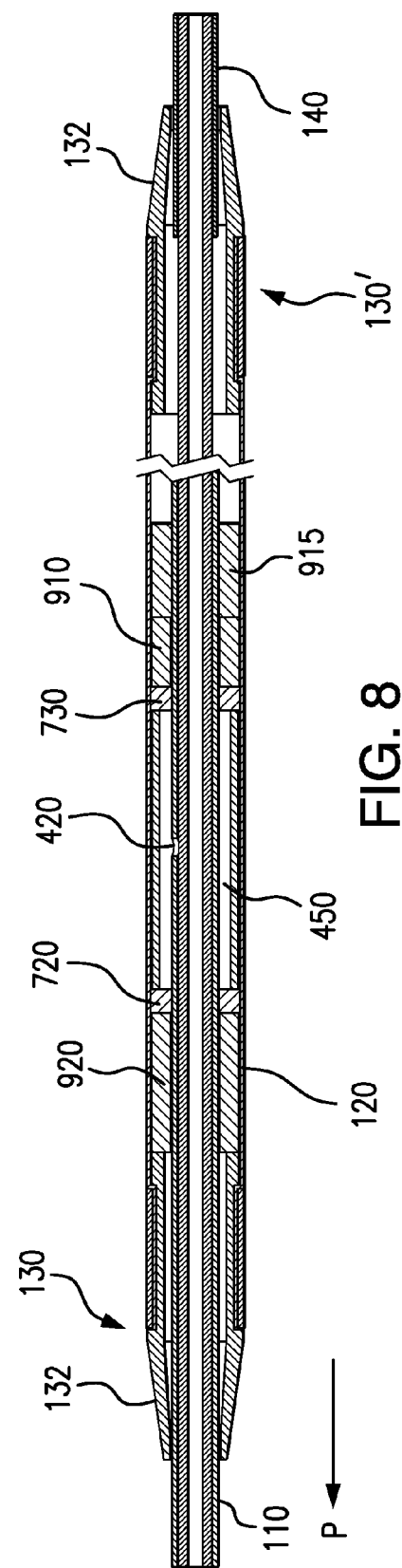
FIG. 8 is a cross sectional view of a catheter having a pressure chamber with proximal and distal movable tubular structures, in accordance with another representative embodiment of the disclosed subject matter.

The movable tubular structure can be disposed along the catheter at any suitable location, depending upon the desired functions and need. The catheter can additionally include more than one movable tubular structure. For example, and as embodied herein, as depicted in FIGS. 4-7, the movable tubular structure 130 can be disposed at the proximal end of the outer tubular member 120. In this embodiment, the movable tubular structure includes a taper segment 132 extending from the proximal end of the outer tubular member 120. The catheter of FIGS. 4, 6, and 7 only includes one movable tubular structure 130. Alternatively, or in addition thereto, the movable tubular structure can be disposed at the distal end of the outer tubular member 120. In the embodiment of FIG. 8, the catheter includes both a proximal movable tubular structure 130 and a distal movable tubular structure 130'. The distal movable tubular structure 130' has a taper segment 132 extending from the distal end of the outer tubular member.

The movable tubular structure can comprise or be made of any suitable biocompatible material, such as PEEK. Because it is not necessary to bond the outer tubular member directly to the movable tubular structure, the movable tubular structure can comprise a material incompatible for thermal bonding with the material of the outer tubular member. As such, it is beneficial for the movable tubular structure to be made of a suitable material having a higher melt temperature than that of the outer tubular member and/or filler Thus, even upon application of thermal energy or heat to the area of the movable tubular structure, the movable tubular structure can maintain its structural integrity. The movable tubular structure can further include a PTFE liner or other low friction or lubricious layer, if desired.

Figure 9:
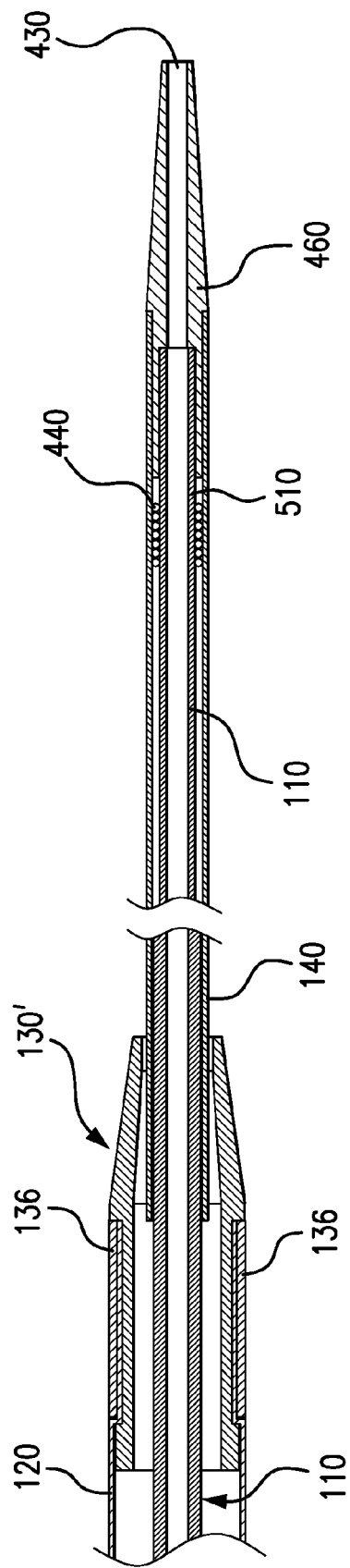
FIG. 9 is a cross sectional view of a catheter having a distal movable tubular structure couple the outer tubular member with a distal sheath, in accordance with yet another representative embodiment of the disclosed subject matter.

In accordance with another aspect of the disclosed subject matter, a distal sheath can be provided, coupled to the outer tubular member by the movable tubular structure. For purpose of illustration, and not limitations, FIG. 9 depicts a catheter having a distal movable tubular structure and distal sheath. As embodied here, the catheter comprises a distal sheath 140 coupled to the outer tubular member 120 by the distal movable tubular member 130'. The distal sheath 140 is thus movable with the outer tubular member 120 and the proximal movable tubular member 130. Accordingly, the distal sheath 140 is movable relative the inner tubular member 110 by movement of the outer tubular member 120. As depicted, the distal sheath 140 can have an outer cross dimension less than an outer cross dimension of the outer tubular member 120. For example, and for use in neuro indications the outer cross dimension of the sheath 140 can be between approximately 4 French to approximately 6 French whereas the distal sheath has an outer cross dimensions of from approximately 0.002 inches to approximately 0.003 inches. The smaller dimension of the sheath 140 allows the sheath to have a flexibility and a stiffness different than a flexibility and stiffness of the outer tubular member 120. In one embodiment, such as for neuro indications, the catheter at the distal end along the sheath 140 has a greater flexibility and less stiffness than the catheter along the outer tubular member 120. In another embodiment, such as for peripheral indications, such as below-the-knee procedures, the catheter can have less flexibility and greater stiffness at a distal end e.g., to allow the distal tip to ease through calcified lesions. The distal sheath thus can be made of the same material as the outer tubular member, or can be made of a different suitable material depending upon the intended purpose. For example, the distal sheath for neuro indications can comprise a more flexible softer material that a distal sheath for a below-the-knee indication.

A variety of configurations of the movable tubular structure can be provided to couple the outer tubular member with the distal sheath. For purpose of illustration, and not limitation, and with reference to FIG. 5C, the movable tubular structure can comprise a body member having a base segment with a first recess defined therein and a taper segment with a second recess defined therein. In this manner, the outer tubular member can be coupled to the base segment of the movable tubular structure by a filler as described above. Similarly, a portion of the distal sheath can be disposed within the second recess of the tapered segment of the movable tubular structure, and then a filler of suitable material can be disposed in the trough formed by the distal sheath in the second recess to couple the distal sheath to the moveable tubular structure in a similar manner. Although, the distal sheath can be coupled directly as shown in FIGS. 8-9.

As previously noted, and as embodied in FIGS. 4-7 and 9, the catheter can be used for the delivery of medical devices, such as stent 440, disposed along the length of the catheter. The catheter embodied herein includes stent seat 510 for the initial placement of the stent 440. The stent seat 510 can be disposed proximate the distal end portion of the inner tubular member. However, depending on the intended use and indication, the stent 440 and stent seat 510 can be located at other suitable locations along the catheter for the desired indication. For example, for cardiovascular indications, such as within the heart, the stent and the stent seat can be disposed at the distal end of the catheter. As embodied in FIGS. 4-7, the stent seat 510 and the stent 440 are disposed at the distal end of the catheter with the outer tubular member 120 retaining the stent 440 at the stent seat. For neuro indications, such as procedures in the brain, the stent seat and the stent can be disposed distal to the outer tubular member at the distal end of the catheter. As embodied in FIG. 9, the distal movable tubular structure 130' couples a distal sheath 140 of smaller cross section with the outer tubular member 120. In this embodiment, the distal sheath 140 retains the stent 440 at the stent seat 410 and the catheter has a smaller cross dimension at the distal end for neuro application. Although reference is made to a stent and stent seat, for purpose of illustration it is recognized that other medical devices also can be delivered by and deployed from the catheter of the disclosed subject matter.

Figure 10:
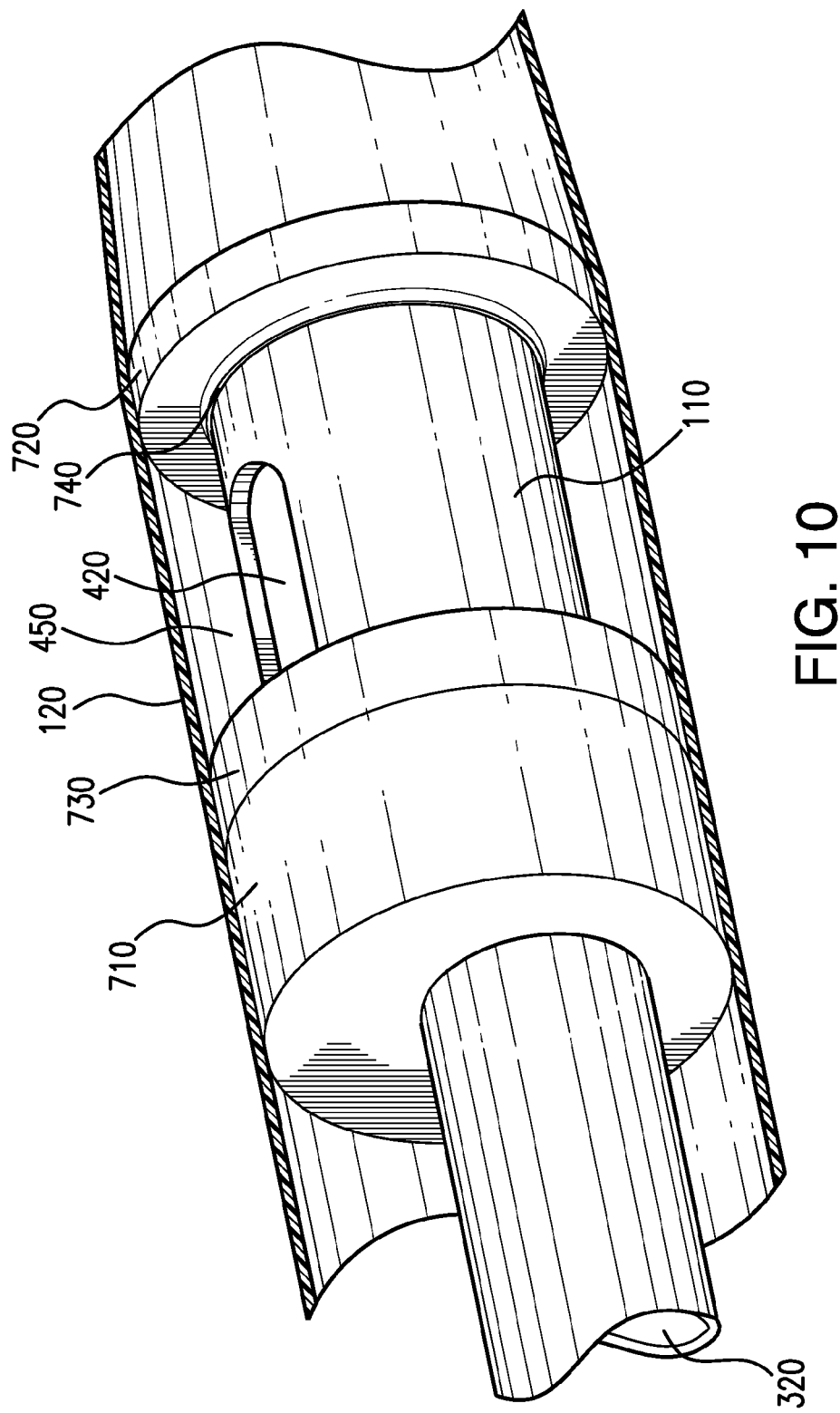
FIG. 10 is a detail perspective view of the catheter of FIG. 4 along line FIG. 10.
Figure 11:
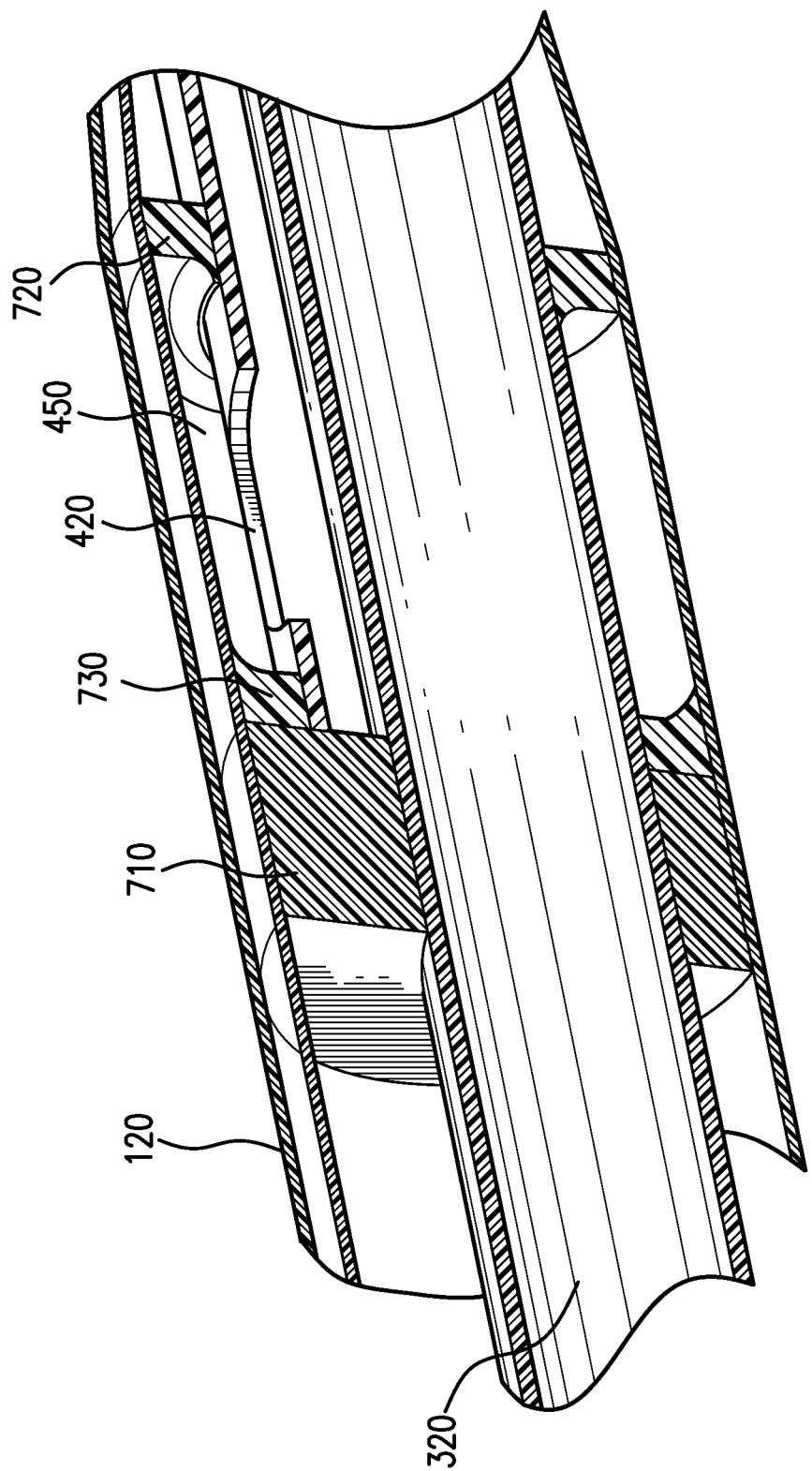
FIG. 11 is a cross sectional perspective view of the detail of FIG. 10.

As previously discussed, the outer tubular member 120, and the movable tubular structure 130, as well as the distal the sheath 140, if provided, are movable with respect to the inner tubular member 110, such as to release a stent 440 retained on the catheter at the stent seat 510. To initiate movement of the components of the catheter, a suitable actuator is provided. For example, and in accordance with another aspect, the catheter can further include a hydraulic pressure chamber. Examples of suitable hydraulic pressure chambers include U.S. application Ser. No. 13/467,660, entitled "Catheter Having Hydraulic Actuator" assigned to Abbott Cardiovascular Systems Inc.; U.S. application Ser. No. 13/467,715, entitled "Catheter Hydraulic Actuator with Tandem Chambers" assigned to Abbott Cardiovascular Systems Inc.; and U.S. application Ser. No. 13/467,679, entitled "Catheter Having Dual Balloon Hydraulic Actuator" assigned to Abbott Cardiovascular Systems Inc., the contents of each of which is incorporated herein by reference in its entirety:

Solely for purpose of illustration, FIGS. 10 and 11 depict the pressure chamber 450, which is defined between proximal seal 720 and distal seal 730. For purposes of discussion and illustration, other features of the catheter and the pressure chamber are not illustrated herein, but can be understood from the more detailed descriptions incorporated by reference herein. The proximal seal 720 extends from the interior surface of the outer tubular member 120 toward the exterior surface of the inner tubular member 110 and is located proximal to fluid flow port 420. The proximal seal 720 is fixed to the interior surface of the outer tubular member 120 and moves freely relative to the inner tubular member 110. With reference to the embodiment of FIG. 4, the proximal seal 720 is disposed distal to the movable tubular structure 130.

FIGS. 10 and 11 further depict distal seal 730 spaced from the proximal seal 720. The distal seal 730 extends from the exterior surface of the inner tubular member 110 toward the interior surface of the outer tubular member 120 and is located distal to fluid flow port 420. The distal seal 730 is fixed to the exterior surface of the inner tubular member 110 and moves freely relative to the interior surface of the outer tubular member 120. In this manner, the outer tubular member 120 moves freely relative to the distal seal 730. As embodied herein, and as shown in FIG. 9, one or both of the proximal and distal seal can form a wiper seal 740 across the corresponding surface. As such, and as depicted in FIGS. 10 and 11, the pressure chamber is defined by the proximal seal 720, distal seal 730, the exterior surface 111 of the inner tubular member 110, and the interior surface 121 of the outer tubular member 120. Pressure chamber 450 is in fluid communication with fluid flow port 420.

As recognized in the art, the outer tubular member 120 constrains the medical device to be delivered. The medical device, e.g., a self expanding stent, is deployed by retracting the outer tubular member 120 (catheter sheath). In other embodiments, as previously discussed with respect to FIGS. 8-9, the outer tubular member 120 is connected to sheath 140 via a movable tubular structure 130. The distal sheath 140 retains the stent and the stent is deployed by retracting the outer tubular member 120 along with the distal sheath 140. Retraction is achieved by the introduction of fluid under pressure through the fluid lumen 310 using a conventional device, such as an indeflator or a syringe. The indeflator can include a threaded engagement or other locking mechanism to control pressurization and depressurization of the pressure chamber (not shown). Additionally, a pressure gauge can be provided with the indeflator to monitor the pressure system of the catheter. The indeflator can be configured to allow for the rapid release of hydraulic pressure to stop or inhibit the deployment of the stent. The indeflator can also be configured to create and/or maintain negative pressure in the catheter. The indeflator can further create a vacuum that decreases the profile of the catheter. For example, by creating a vacuum, the outer tubular member 120 disclosed herein, can be configured to decrease in profile and/or lock in position. An example of a suitable indeflator is an Atrion indeflator Atrion Medical-55 ATM.

An adapter can be provided at the proximal end of the catheter for access to the fluid lumen and can be configured for connecting to a fluid source (not shown). With reference to FIG. 10, fluid is introduced into the fluid lumen and exits the fluid lumen at flow port 420 and fills pressure chamber 450. Once sufficient fluid is introduced into the pressure chamber 450, a force is applied on the distal and proximal seals. Because the distal seal 730 is fixed relative to the inner member, only the proximal seal 720 and outer tubular member 120 attached thereto is capable of movement relative to the inner member in the proximal direction P. Movement of the proximal seal 720 upon the application of force in the pressure chamber 450 urges the outer tubular member 120, along with the movable tubular structure 130 and distal sheath 140 if provided, to move in the proximal direction P along the inner tubular member thereby allowing the medical device to be deployed. Distal seal 730, as embodied herein, is configured as a wiper-seal with the interior surface of outer tubular member 120. The outer tubular member 120, and the movable tubular structure 130 and sheath 140 if provided, thus move relative to distal seal 730. Proximal seal 720 mounted to the interior surface of outer tubular member 120 is configured as a wiper-seal with the exterior surface 111 of inner tubular member 110. The proximal seal 720 is free to move relative to the inner tubular member 110.

Furthermore, by providing a movable tubular structure 130 and distal sheath 140, the pressure chamber 450 can be sufficiently spaced proximal to the distal end of the catheter and the stent seat for neuro indications or the like. Thus, the pressure chamber 450 can be disposed at the proximal portion of the catheter. For instance, the pressure chamber 450 can be spaced approximately 8 inches to approximately 20 inches from the stent 410 and stent seat 510. This spaced relationship between the pressure chamber to the stent provides certain safety benefits if a mechanical issue arises within the pressure chamber; e.g., maintains spaced relations from the brain.

Although shown as a single piece seal construction in FIGS. 10 and 11, each seal of the disclosed subject matter can be a multi-piece seal assembly, if desired. For example, the seal assembly can include a seal member and a bushing to provide a backing to the seal member, as known in the art. As depicted in FIG. 8, the seals 720 and 730 can further be supported by a spacer device, such as proximal and distal bushings 920 and 910, respectively. In the embodiment of FIG. 8, the proximal bushing 920 is disposed external to the pressure chamber, such as between the proximal seal 720 the proximal movable tubular structure 130 and the distal bushing 910 is disposed external to the pressure chamber, such as between the distal seal 730 and the distal movable tubular structure 130. Additional spacer devices can be provided as desired. The catheter can further include a stopper member 915 coupled to the inner tubular member 110 distal to the distal seal 730 for additional support. In FIG. 8, a bushing 910 is disposed between the distal seal 730 and the stopper member 915. The stopper and bushings can be constructed of any suitable material, including, but not limited to, PEEK, Pebax, HDPE, LDPE, a mixture of HDPE and LDPE, a Nylon blend such as L75/L25, or the like. Furthermore, the bushings can comprise a metallic material, combination low density polyethelene, silicon, nitril, soft Pebax 30, or other blends of suitable material, and can be coated with a suitable material as known in the art, and can include a coating.

As relatively high fluid pressures are needed to retract outer tubular member 120, the pressure chamber is formed to withstand such pressures with minimal to no leaks. A variety of suitable seal constructions and materials can be used, such as, but not limited to, sliding seals, rings, cups seals, lips seals, and compressed bushings. For example, each seal can be formed as a separate member and attached to the corresponding tube member, or can be formed as part of the tubular member. Solely for purposes of illustration, a hydrophilic material, such as but not limited to, HydroMed™, Hydrothane™, Hydak®, can be used for the seals. Seals made of such material can be configured to swell when exposed to an aqueous environment, thus sealing more tightly while maintaining lubricity. The seals thus can comprise an expandable material or composite of materials to increase accordingly to match the dimensions of the outer tubular member. That is, the seal can be configured to expand with the outer tubular member to maintain an adequate seal.

As the pressure chamber expands, the exposed surface area of the seal can also increase, resulting in a proportional increase in retraction force at a given fluid pressure. Thus, an expanding pressure chamber provides for greater retraction force at a given pressure. Seals made of such material can be configured to swell when exposed to an aqueous environment, thus sealing more tightly while maintaining lubricity. Alternatively, the proximal and distal seals can be coated with a hydrophobic layer such as oil or wax or made of hydrophobic material such as a fluorocarbon or olefins like polypropylene to be used with a suitable pressurized fluid, to prevent swelling of the seals. Solely for example, silicone seals can be provided with a Hydromer 2314-172 coating. In another embodiment, O-rings can be used for the seal constructions comprised of silicone, buna, or other suitable elastomers. Furthermore, solely for purpose of example, the seal can include soft tubing such as a low durometer Pebax. Additionally or alternatively, a high viscosity hydraulic fluid can be used to inhibit leaks.

Embodiments of the disclosed subject matter allow the pressure chamber to operate with a variety of different suitable pressures. Solely for purpose of example, in one embodiment the pressure chamber can handle a positive pressure of up to 750 psi, and a negative pressure of approximately 14 psi. An exemplary operating parameter for a cardiovascular catheter indications can operate at pressures ranging up to approximately 40 to 50 ATM (or about 588-735 psi).

In accordance with another aspect, the catheter further can include bellows, or a bladder component (not shown) within the chamber to prevent leaks. The bellows or bladder component is attached to the exterior surface of the inner tubular member and is in fluid communication with the fluid flow port, wherein fluid introduced through the fluid flow port expands the bellows component to further retract the outer tubular member.

In yet another aspect of the disclosed subject matter, spacer elements (not shown) can be provided within the pressure chamber. The spacer elements can prevent the outer tubular member, proximal seal and distal seal from being collapsed during delivery and storage of the catheter. The spacer elements can also reduce the amount of fluid needed to retract the outer tubular member. The spacer elements can be made of any of a variety of suitable shapes and materials, such as ring members having diameters corresponding to the inner and outer diameters of the inner and outer tubular members, respectively.

If desired, the distal seal can form a bumper or stop member for the medical device, such as a stent. In other embodiments, the pressure chamber 450 is spaced from the medical device to be delivered, such as by the use of a distal sheath as previously discussed herein. Alternatively, in accordance with another aspect of the disclosed subject matter, the catheter can include a stop 710 secured to the inner tubular member 110, as depicted in FIGS. 10 and 11. The stop is disposed distal to the pressure chamber 450 and proximal to the medical device to be delivered, e.g., the stent. In this manner, the stop 710 seals the hydraulic fluid lumen 310 but allows the guidewire tube 321 and/or guidewire (not shown) to pass through. Stop 710 can be made of or include a radiopaque material to provide the physician performing the procedure with visibility as to placement of the catheter so that the medical device can accurately be positioned at the treatment site. The stop 710 is thus a radiopaque marker. For example, the marker can be a radiopaque metallic ring, or made of a tungsten loaded polymer for increased softness and flexibility. Other suitable markers known can be used.

In accordance with another aspect of the disclosed subject matter, other devices, such as a spring, can be provided to bias the outer tubular member 120 in the proximal direction P. Examples of springs and other devices that can be implemented with embodiments of the subject matter can be found in U.S. application Ser. No. 13/467,660, entitled "Catheter having Hydraulic Actuator" by Michael Bialas and Michael Green and owned by Abbott Cardiovascular Systems Inc.; U.S. application Ser. No. 13/467,679, entitled "Catheter having Dual Balloon Hydraulic Actuator" by Michael Green and Michael Bialas and owned by Abbott Cardiovascular Systems Inc.; and U.S. application Ser. No. 13/467,715, entitled "Catheter having Hydraulic Actuator with Tandem Chambers" by Michael Green and Michael Bialas, the contents of which are herein incorporated by reference in their entirety.

Reference is now made to FIG. 7, solely for purposes of illustration, which depicts an over-the-wire variation of the disclosed subject matter. In this embodiment, catheter 100 includes inner tubular member 110, outer tubular member 120 (shown in a retracted position), a guidewire lumen 320, and fluid lumen 310 having fluid flow port 420. Catheter 100 further includes medical devices, such as stent 440 as shown in an expanded state, stent seat 510, and a distal guidewire port 430.

As shown in FIG. 7A, solely for the purpose of illustration, the inner tubular member 110 or elongated catheter shaft of the catheter can include first and second tubular members 110 and 610, respectively, in coaxial relationship with each other to define a central guidewire lumen 320 within the first tubular member 110 and an annular fluid lumen 310 located between the first and second tubular members 610 of the inner tubular member or shaft. The fluid lumen 310 can supply a hydraulic medium under positive pressure and can withdraw the hydraulic medium, i.e., provide negative pressure, from pressure chamber 450 as desired. The catheter is sized and configured for delivery within a corresponding body lumen for the intended indication, such as a vasculature for vascular intervention. The catheter includes a guidewire lumen for delivery over a guidewire 620 as shown in FIG. 7A. For example, in one embodiment such as for neuro indications, the catheter can be 0.012 or 0.010 guidewire compatible. The portion of the inner tubular member extending distal of the chamber can be defined by an extension of the first tubular member 110, or an extension of the second tubular member 610, or by a separate tubular member as desired. Although a coaxial shaft and over-the-wire (OTW) catheter configuration is depicted in FIG. 7, those skilled in the art will recognize that other configurations and known materials of construction can be used without departing from the scope of the disclosed subject matter, for example, the rapid exchange and/or dual lumen configurations as previously described.

The pressure chamber 450 can additionally include a locking system to prevent the outer tubular member 120 from prematurely moving in the proximal direction P. The pressure chamber 450 with the locking system operates substantially the same as previously described. However, the locking system restricts the initial movement of the outer tubular member until suitable pressure is first introduced into the chamber. Examples of suitable locking systems can be found in the currently pending application entitled, "Catheter Having Hydraulic Actuator And Locking System", assigned to Abbott Cardiovascular Systems Inc. and filed on the same day as the present application, the contents of which are incorporated by reference herein in its entirety.

In accordance with another aspect of the disclosed subject matter, a method of making a catheter is furthermore disclosed. The method includes, among other things, providing an inner tubular member having a proximal end portion, a distal end portion and an exterior surface. The inner tubular member further has a guidewire lumen defined therein. An outer tubular member movable relative to the inner tubular member is provided. The outer tubular member has a proximal end, a distal end and an interior surface directed toward the exterior surface of the inner tubular member.

Details regarding the material of the disclosed subject are understood from the detailed description above. Generally, however, a movable tubular structure is located between the outer tubular member and the inner tubular member. The movable tubular structure includes a body member having an outer surface with a recess defined therein. The outer tubular member is received within the recess to form a trough along a portion of an exterior surface of the outer tubular member. A filler is disposed in the trough. The filler has a suitable hoop strength to couple the outer tubular member to the body member of the movable tubular structure. As indicated above, the filler can be any of a variety of suitable materials. For example, if a thermally compatible material is provided to bond with the outer tubular member, then the method can further include providing a shrink wrap over the filler at the trough. The filler is thermally bonded with the outer tubular member to secure the outer tubular member with the movable tubular structure and the shrink wrap is removed. A similar method can be used to couple the distal sheath if provided, to the movable tubular structure. Other bonding techniques are further contemplated herein, as previously discussed.

In accordance with the embodiments of the subject matter previously described, the components of the catheter can be made of a variety of suitable materials. For example, the proximal and distal seals of the expandable chamber configuration can be formed of any suitable materials. Solely for example, the seals can be rubber or silicon. In embodiments having an expandable pressure chamber, the seals can be formed of a low durometer rubber having a compressed condition and an expanded condition. The seals can be significantly compressed and deformed in the initial delivery configuration, transitioning to the expanded condition when the pressure chamber is pressurized. Alternatively, the seals can be made of hydrophilic polymers that absorb fluid in the pressure chamber and expand along with the outer tubular member. Alternatively, the proximal and distal seals can be made of hydrophobic material.

The inner tubular member and outer tubular member each can be a single piece construction, or an assembly of components, and can be made of any suitable material. For example, suitable materials include, but are not limited to polymer materials such as nylon, urethane, polyurethane, PEEK, PTFE, PVDF, fluoropolymer such as Kynar, PE, HDPE, a trilayer material including L25, Plexar, PEBAX, or polyethylene of various suitable densities. For example, the outer tubular member can comprise a nylon braided tube with a PTFE liner. Additionally a lubricious liner, such as PTFE, on the inside diameter of the outer tubular member, or the sheath, allows the stent to deploy with low force and can prevent the outer tubular member from being bonded to the stent or other catheter components. In another example, the outer tubular member includes a fluoropolymer braided tube with lubricous liner. Furthermore, at least a portion of the inner and/or outer tubular members can be constructed of an alloy or metallic material, such as stainless steel hypodermic tubing or the like.

As a further alternative, the inner tubular member and/or the outer member each can be constructed of multiple outer tubular members. A stop can further form a joint for two adjacent tubular members. The outer tubular member can further be constructed of a composite comprising a fabrication of several different materials, such as a co-extrusion of different polymers, or a fiber-reinforced composite material such as fiber reinforced resin materials or braided materials. Solely for example, exemplary embodiments can include a braided tube with a PTFE liner, a Polymide middle layer with braiding and a Pebax 72D outer layer. Additionally, to improve flexibility, helical or spiral member configurations can be used in the construction of the inner and outer tubular members.

Exemplary constructions for the outer tubular member include a single layer of polyimide or PEEK; a trilayer material of L25, Plexar, HDPE; or a braided tube with a PTFE liner, a Polyimide middle layer braiding middle layer, and a Pebax 72D outer layer. The inner and/or outer tubular members can also be reinforced by the addition of a strengthening member, such as, for example, a wire coil. In one embodiment, the inner tubular member is reinforced by the addition of a strengthening member along a length corresponding to the pressure chamber.

It is further contemplated that the inner and outer tubular members can be constructed of other biocompatible material. As such, the inner and outer tubular members of the catheter can be constructed from the above-identified polymers, combinations or blends of these polymers, whether alone or in combination with other materials, or other bioabsorbable materials.

The inner and outer tubular members can be manufactured using a variety of known techniques such as but not limited to: extrusion, injection molding, air-blowing, stretching, deep drawing, polymerization, cross-linking, dipping from solution, powder depositioning, sintering, electro-spinning, melt spinning, deformation under temperature, stretch blowing, chemical grafting any combination of the above with reinforcement element like metal braids, coils, glass fibers, carbon fibers and other kind of organic or inorganic fibers, liquid crystals, as well as classical machining technologies like milling, drilling, grinding, etc. In the event that metallic elements such as hypotubes are to be incorporated, various metallic manufacturing techniques can be used, such as but not limited to, machining, tube drawing processes, drilling, milling, EDM, other deformation methods, plating, sputtering, electrografting, sintering, and depositioning e-polishing, among others. In one embodiment of the disclosed subject matter, the inner tubular member includes a stainless steel hypotube at least at its proximal end.

Additionally, the inner and outer tubular members can be constructed from PE, polypropylene, Kynar, or urethane by an extrusion process using an extruder such as that available from any of a number of known suppliers. The materials can be post-processed in a number of ways including, for example and not by way of limitation, extrusion, molding, such as by injection or dipping, textile processing such as weaving or braiding, and forming. Forming processes that can be suitable are rolling and welding sheets of material or vacuum forming into tubular shapes, to name only a few examples.

The inner and outer tubular members can be further coated with any of a variety of materials and techniques to enhance performance if desired, including a number of suitable coatings and coating techniques subject to patent matters owned by Abbott Laboratories such as U.S. Pat. Nos. 6,541,116, 6,287,285, and 6,541,116, the entireties of which are hereby incorporated by reference. For example, possible coating materials include lubricious materials such as Teflon®, and hydrophobic materials such as silicone lubricant dispersion PN 4097, or hydrophilic materials such as hydrogel, or lubricious coatings.

The inner and outer tubular members can have any suitable cross-sectional shape, including elliptical, polygon, or prismatic, although a circular cross-section generally is preferred. The inner and outer tubular members can also have any suitable size and diameter depending upon the desired application. The catheter is suitably sized and configured for delivery within a corresponding body lumen for the intended indication, such as a vasculature for vascular intervention.

According to one embodiment, the outer tubular member can include an outer layer and an inner layer. The outer tubular member can be provided with an inner layer attached to or formed with an outer layer. The inner layer or liner can include a lubricious material to facilitate the sliding of the outer tubular member in a proximal direction when the outer tubular member is retracted. For example, different types of polymers such as PTFE or high-density polyethylene (HDPE) can be used for the inner layer. Additionally, other lubricious polymers can be used. The outer layer, as embodied herein, provides sufficient strength to capture a medical device therein, as well as allow movement between the first position and the second position. The multiple layers can be formed separately and adhered or bonded together or co-extruded as a single member.

In further accordance with the disclosed subject matter the outer tubular member can include a reinforcing layer disposed between the outer layer and the inner layer, such as a braided material. For example, the reinforcing layer can be provided in the form of a braided stainless steel tube or sheet or the like. The braid can include flattened filaments, as opposed to having filaments with a round cross-section. Alternatively, the reinforcement can be in the form of a tube including woven fabric or appropriately oriented filaments, such as carbon fibers encased in a polymeric matrix. Likewise, such reinforcing fibers could additionally or alternatively be incorporated into inner layer and/or outer layer during the manufacturing process.

When the outer tubular member is provided with an inner layer, outer layer and a reinforcing layer, the outer tubular member can be formed in the following manner. First, inner layer is formed through a tubular extrusion process, and disposed about a forming mandrel (not shown). The forming mandrel, as embodied herein, has a shape that corresponds to the desired shape of the inside of the outer tubular member. Next, the reinforcing layer, which can be provided in the form of a stainless steel braid material, is positioned over a predetermined length of inner layer. Next, the outer layer is extruded and positioned over the reinforcing layer. The outer layer can be provided in the form of two separate tubular members that are overlapped slightly at their ends over reinforcing layer. Each portion of outer layer can be a different material selected to provide a different durometer as described above. The two portions of outer layer can overlap by an amount such as approximately 0.1 inches. Next, a sleeve of heat shrinkable material is positioned over the entire outer tubular member assembly. Finally, heat is applied to the assembly. When heat is applied, the heat shrinkable tubing shrinks, and causes inner layer to fuse with outer layer, trapping reinforcing layer therebetween. The heating process also causes inner layer to conform to the shape of the forming mandrel. After the assembly cools, the heat shrinkable tubing is cut away, leaving behind the outer tubular member.

While the disclosed subject matter is described herein in terms of certain preferred embodiments, those skilled in the art will recognize that various modifications and improvements can be made to the disclosed subject matter without departing from the scope thereof. Additional features known in the art likewise can be incorporated, such as disclosed in U.S. Pat. No. 7,799,065 to Pappas, which is incorporated in its entirety by reference herein. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Furthermore, although reference is made to a stent throughout this disclosure, other suitable devices and implants likewise can be delivered using the catheter and system disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A catheter system comprising:
an inner tubular member having a proximal end portion, a distal end portion and an exterior surface, the inner tubular member further having a guidewire lumen defined therein;
an outer tubular member movable relative to the inner tubular member, the outer tubular member having a proximal end, a distal end and an interior surface directed toward the exterior surface of the inner tubular member; and
a movable tubular structure movable with the outer tubular member relative to the inner tubular member, the movable tubular structure being at least partially disposed between the outer tubular member and the inner tubular member, the movable tubular structure comprising a body member including a taper segment and a base segment, the taper segment extending proximally from the proximal end of the outer tubular member or distally from the distal end of the outer tubular member, wherein the body member has an outer surface with a recess defined therein, the outer tubular member received within the recess to form a trough along a portion of an exterior surface of the outer tubular member, the trough having a filler disposed therein to couple the outer tubular member to the body member of the movable tubular structure.

2. The catheter system according to claim 1, wherein the recess is disposed in the base segment of the body member.

3. The catheter system according to claim 1, wherein the recess is disposed in the taper segment of the body member.

4. The catheter system according to claim 1, wherein the recess has a depth, wherein the depth of the recess is approximately equal to or greater than a thickness of the outer tubular member.

5. The catheter system according to claim 4, wherein the filler has a thickness comprising the depth of the recess less the thickness of the outer tubular member.

6. The catheter system according to claim 4, wherein an exterior surface of the filler is substantially flush with the exterior surface of the outer tubular member adjacent the recess.

7. The catheter system according to claim 6, wherein a transition between the exterior surface of the filler and the exterior surface of outer tubular member adjacent the recess is substantially smooth.

8. The catheter system according to claim 1, wherein the recess is defined in part by a shoulder, wherein the shoulder has an angle relative the outer surface.

9. The catheter system according to claim 8, wherein the angle ranges from approximately 70 degrees to approximately 110 degrees.

10. The catheter system according to claim 1, wherein the body member includes a second recess defined therein with a second portion of the outer tubular member received within the second recess.

11. The catheter system according to claim 1, wherein the filler comprises a material compatible for thermal bonding with a material of the outer tubular member.

12. The catheter system according to claim 11, wherein the filler is bonded to the outer tubular member by at least one of heat bonding, thermal bonding, or adhesive bonding.

13. The catheter system according to claim 11, wherein the material of the filler comprises the material of the outer tubular member.

14. The catheter system according to claim 1, wherein the filler comprises at least one of nylon, fluoropolymer, peek, epoxy, platinum iridium, ceramic, and metal.

15. The catheter system according to claim 1, wherein the filler has a suitable hoop strength to couple the outer tubular member with the recess of the movable tubular member.

16. The catheter system according to claim 1, wherein the outer tubular member comprises at least one of a nylon braided tube with a lubricious liner or a fluoropolymer braided tube with a lubricious liner.

17. The catheter system according to claim 1, wherein the movable tubular structure includes a PTFE liner.

18. The catheter system according to claim 1, wherein the movable tubular structure comprises a biocompatible material with a melting temperature greater than the filler.

19. The catheter system according to claim 1, wherein the movable tubular structure is disposed at the proximal end of the outer tubular member.

20. The catheter system according to claim 19, wherein the taper segment extends proximally from the proximal end of the outer tubular member.

21. The catheter system according to claim 1, wherein the inner tubular member has a fluid lumen defined therein, the fluid lumen having a fluid flow port defined by the exterior surface of the inner tubular member along the distal end portion of the inner tubular member, the catheter further comprising:
   a proximal seal extending from the interior surface of the outer tubular member toward the exterior surface of the inner tubular member, the proximal seal located proximal to the fluid flow port;
   a distal seal extending from the exterior surface of the inner tubular member toward the interior surface of the outer tubular member, the distal seal located distal to the fluid flow port; and
   a pressure chamber defined by the proximal seal, the distal seal, the exterior surface of the inner tubular member, and the interior surface of the outer tubular member, with the pressure chamber in fluid communication with the fluid flow port, wherein fluid introduced through the fluid flow port and into the pressure chamber applies a force on the proximal seal to urge the outer tubular member and the movable tubular structure in a proximal direction.

22. The catheter system according to claim 21, wherein the proximal seal is distal to the movable tubular structure.

23. The catheter system according to claim 22, further comprising a spacer device disposed between the proximal seal and the movable tubular structure.

24. The catheter system according to claim 23, wherein the spacer device comprises at least one bushing.

25. The catheter system according to claim 21, further comprising a stopper member coupled to the inner tubular member distal to the distal seal.

26. The catheter system according to claim 25, further comprising a bushing disposed between the distal seal and the stopper member.

27. The catheter system according to claim 1, wherein the inner tubular member further includes a distal tip.

28. The catheter system according to claim 1, further comprising a stent seat disposed proximate the distal end portion of the inner tubular member.

29. The catheter system according to claim 28, further comprising a stent positioned at the stent seat.

30. The catheter system according to claim 1, wherein the movable tubular structure is disposed at the distal end of the outer tubular member.

31. The catheter system according to claim 30, wherein the taper segment extends distally from the distal end of the outer tubular member.

32. The catheter system according to claim 30, further comprising a distal sheath coupled to the outer tubular member by the movable tubular member, the distal sheath being movable relative the inner tubular member by movement of the outer tubular member.

33. The catheter system according to claim 32, wherein the distal sheath has an outer cross dimension less than an outer cross dimension of the outer tubular member.

34. The catheter system according to claim 33, wherein the outer cross dimension of the distal sheath is between approximately 4 French to approximately 6 French.

35. The catheter system according to claim 32, wherein the distal sheath has a flexibility and a stiffness different than a flexibility and stiffness of the outer tubular member.

36. A method of making a catheter comprising:
   providing an inner tubular member having a proximal end portion, a distal end portion and an exterior surface, the inner tubular member further having a guidewire lumen defined therein;
   providing an outer tubular member movable relative to the inner tubular member, the outer tubular member having a proximal end, a distal end and an interior surface directed toward the exterior surface of the inner tubular member;
   locating a movable tubular structure at least partially between the outer tubular member and the inner tubular member, the movable tubular structure comprising a body member including a taper segment and a base segment, the taper segment extending proximally from the proximal end of the outer tubular member or distally from the distal end of the outer tubular member, wherein the body member has an outer surface with a recess defined therein, the outer tubular member being received within the recess to form a trough along a portion of an exterior surface of the outer tubular member; and
   disposing a filler in the trough, the filler having a suitable hoop strength to couple the outer tubular member to the body member of the movable tubular structure, wherein the movable tubular structure is movable with the outer tubular member relative to the inner tubular member.

37. The method according to claim 36, further comprising:
   providing a shrink wrap over the filler at the trough;
   thermally bonding the filler with the outer tubular member to secure the outer tubular member with the movable tubular structure; and
   removing the shrink wrap.

* * * * *